United States Patent [19]

Orr et al.

[11] Patent Number: 5,298,236

[45] Date of Patent: Mar. 29, 1994

[54] LIQUID ANTIPERSPIRANT COMPOSITION

[75] Inventors: Thomas V. Orr; Patricia J. Newcomer, both of Cincinnati, Ohio

[73] Assignee: The Procter & Gamble Company, Cincinnati, Ohio

[21] Appl. No.: 28,754

[22] Filed: Mar. 9, 1993

Related U.S. Application Data

[63] Continuation of Ser. No. 611,231, Nov. 8, 1990, abandoned.

[51] Int. Cl.$^5$ .......................... A61K 7/34; A61K 7/36; A61K 7/38; A61K 9/12
[52] U.S. Cl. ........................................ 424/47; 424/65; 424/66; 424/67; 424/68
[58] Field of Search .............................. 424/66, 68, 47

[56] References Cited

U.S. PATENT DOCUMENTS 4,777,035 10/1988 Shin ........................................ 424/66

Primary Examiner—Dale R. Ore
Attorney, Agent, or Firm—Leonard W. Lewis; Steven J. Goldstein

[57] ABSTRACT

Disclosed are liquid antiperspirant compositions useful for both roll-on and aerosol antiperspirant applications. The compositions have reduced incidence of in-use skin irritation. The compositions comprise from about 10% to about 70%, by weight, of an antiperspirant active material, from about 1% to about 15%, by weight, of a suspension agent, from about 25% to about 75%, by weight, of a non-volatile silicone fluid component, and no more than about 15%, by weight, of volatile silicone fluid. In aerosol embodiments, the compositions can comprise the above composition as a concentrate in combination with an aerosol propellant.

20 Claims, No Drawings

LIQUID ANTIPERSPIRANT COMPOSITION

This is a continuation of application Ser. No. 07/611,231, filed on Nov. 8, 1990 now abandoned.

TECHNICAL FIELD

The present invention relates to liquid antiperspirant compositions containing silicone fluid with reduced incidence of in-use skin irritation. More particularly, this invention relates to liquid antiperspirant compositions containing silicone fluid especially useful for roll-on antiperspirant application with reduced incidence of in-use skin irritation, in combination with excellent cosmetic properties.

BACKGROUND OF THE INVENTION

Antiperspirant compositions have become a part of many persons' personal care and grooming regimen. The antiperspirant active materials which have been typically used include astringent metallic (e.g., aluminum, zinc, and zirconium) salts such as salts of aluminum halides, aluminum hydroxyhalides, zirconyl oxyhalides, zirconyl hydroxyhalides, and complexes of aluminum, zirconium and amino acid (e.g., glycines). These materials, naturally, are sensitive to the presence of water and are preferably stored and delivered to the skin in the substantial absence of water in order to preserve efficacy. Additionally, it is generally perceived as unpleasant for the antiperspirant composition to have a "wet" feel upon application to the skin. Hence, it is also desirable to deliver the antiperspirant active to the skin by a vehicle which minimizes this feeling of wetness. The delivery vehicle must also not cause excessive staining of the user's clothing, and should control or reduce chalky appearance on the skin (and potential rub-off onto the user's clothes) resulting from the antiperspirant active, suspension agent, or other material in the composition. For these reasons, a variety of volatile silicones and non-volatile silicone emollients, and combinations thereof, have commonly been utilized in liquid antiperspirant compositions for delivery of the antiperspirant active material.

The primary silicone material used in recent times for delivery of antiperspirant actives in roll-on liquid antiperspirant applications is volatile cyclomethicone. Volatile cyclomethicone provides a very dry feel upon application and has a low heat of evaporation. The low viscosity of the volatile fluids is also important for providing an easily flowable composition for roll-on or aerosol application. In many of these compositions, a relatively low level of certain non-volatile silicone fluids, or other non-volatile emollient such as paraffin oil (e.g., mineral oil) is also included. These non-volatile fluids generally have a high enough viscosity so that they remain deposited on the skin throughout a significant portion of the day. They also inhibit occurrence of, and consequently rub-off of, chalk-like residue formed from the antiperspirant composition's particulate ingredients. These non-volatile materials are typically utilized at relatively low levels (about 1% to about 12%) to minimize an undesirable "greasy" feel which they can impart.

Liquid roll-on antiperspirant compositions such as these are exemplified in numerous publications including U.S. Pat. No. 4,863,721, Beck et al., issued Sep. 5, 1989. European Patent Application Publication No. 330,140, published Aug. 30, 1989, and U.S. Pat. No. 4,423,041, Clum et al., issued Dec. 27, 1983.

Other liquid emollients have also been used in liquid antiperspirant compositions. These include paraffins such as mineral oil, and a variety of alcohols and esters of alcohols and fatty acids. However, these emollients also have draw-backs which, typically, include skin irritation and greasy feel.

Whereas liquid antiperspirant compositions containing high levels of volatile silicone have provided consumer-acceptable performance and have generally attained a following in the marketplace, the use of such antiperspirant compositions can produce skin irritation in the form of itching, redness, rash, and/or burning (alternately referred to as "stinging"), particularly when applied immediately or soon after shaving. Although the incidence of this is not experienced for all application usages or by all people, it would nevertheless be desirable to provide a liquid antiperspirant composition that could be used for roll-on applications which provide reduced incidence of skin irritation while still providing excellent cosmetic properties, e.g., low "wetness", low levels of "chalky" residue, and low levels of rub-off onto clothing. It would also be desirable to provide liquid antiperspirant compositions useful for aerosol application that have reduced incidence of in-use skin irritation and which retain excellent cosmetic properties. It is an object of this invention to provide such liquid antiperspirant compositions useful for both roll-on and aerosol applications.

SUMMARY OF THE INVENTION

It has been found that by formulation of liquid antiperspirant compositions with high levels of certain non-volatile polysiloxane fluids and low or zero levels of conventional volatile polysiloxane fluids, reduced levels of skin irritation can be attained while maintaining excellent overall cosmetic properties.

Thus, the present invention relates to reduced skin irritation liquid antiperspirant compositions that can be used for roll-on antiperspirant application which comprise an antiperspirant active material and, as the major silicone fluid ingredient, non-volatile polysiloxane fluid having an average viscosity of about 10 centistokes to about 50 centistokes at 25° C. Volatile silicone fluids, such as the cyclic polysiloxanes (e.g., cyclomethicone), can be present, but in keeping with the invention, the level thereof should not exceed about 15%, by weight, of the composition. A suspension agent will also be present in the compositions thereof in an amount sufficient to improve suspendability of the antiperspirant active and thereby enhance consistent, even antiperspirant active delivery to the skin.

In a preferred embodiment for roll-on application, the present invention will encompass liquid antiperspirant compositions comprising:

(a) from about 10% to about 70%, by weight, of a particulate antiperspirant active material;

(b) from about 1% to about 15%, by weight, of a suspension agent component;

(c) from 0% to about 15%, by weight of a volatile silicone; and (d) from about 25% to about 75%, by weight, of a non-volatile silicone fluid component having an average viscosity of from about 10 centistokes to about 50 centistokes at 25° C.

In a preferred embodiment for aerosol application, the present invention will encompass compositions comprising from about 5% to about 80% of a liquid antiperspirant concentrate composition, as described immediately above in (a), (b), (c), and (d), and from about 20% to about 95% of an aerosol propellant.

DETAILED DESCRIPTION OF THE INVENTION

The essential as well as various optional components that can be used in the compositions of the present invention are described below. All percentages given herein are weight percentages of the composition, unless otherwise specifically indicated.

Antiperspirant Active Material

An essential component of the present compositions is an antiperspirant active material. Any particulate compound or composition or mixture thereof having antiperspirant activity can be used. Astringent metallic salts are preferred antiperspirant materials for use herein, particulay including inorganic and organic salts of aluminum, zirconium, and zinc, and mixtures thereof. Particularly preferred are the aluminum and zirconium salts such as aluminum halides, aluminum hydroxy halides, zirconyl oxide halides, and zirconyl hydroxy halides, and complexes of aluminum, zirconium, and/or zinc with amino acids, e.g., glycines.

Specific, exemplary aluminum salts that can be used include aluminum chloride and the aluminum hydroxyhalides having the general formula $Al_2(OH)_aQ_b \cdot XH_2O$ where Q is chloride, bromide, or iodide (preferably chloride); a is from about 2 to about 5, and a+b=about 6, and a and b do not need to be integers; and where X is from about 1 to about 6, and X does not need to be an integer. Particularly preferred are the aluminum chlorhydroxides referred to as "5/6 basic chlorhydroxide" wherein a is 5 and "⅔ basic chlorhydroxide" wherein a is 4. Aluminum salts of this type can be prepared in the manner described more fully in U.S. Pat. No. 3,887,692, Gilman, issued Jun. 3, 1975; U.S. Pat. No. 3,904,741, Jones and Rubino, issued Sep. 9, 1975; U.S. Pat. No. 4,359,456, Gosling et al., issued Nov. 16, 1982; and British Patent Specification 2,048,229, Fitzgerald et al., published Dec. 10, 1980, all incorporated by reference herein. Mixtures of aluminum salts are described in British Patent Specification 1,347,950, Shin, et al., published Feb. 27, 1974, also incorporated by reference herein.

The zirconium compounds which may be used in the present invention include both zirconium oxy salts and zirconium hydroxy salts, also referred to as the zirconyl salts and zirconyl hydroxy salts. These are preferred compounds for use herein and may be represented by the following general empirical formula:

$$ZrO(OH)_{2-nz}B_z$$

wherein z may vary from about 0.9 to about 2 and need not be an integer; n is the valence of B; 2-nz is greater than or equal to 0; and B may be selected from the group consisting of halides (preferably chloride), nitrate, sulfamate, sulfate, and mixtures thereof. Although only zirconium compounds are exemplified in this specification, it will be understood that other Group IVB metal compounds, including hafnium, could be used in the present invention.

As with the basic aluminum compounds discussed above, it will be understood that the above formula is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 2.0 to only slightly greater than 0 groups per molecule.

Several types of antiperspirant complexes utilizing the above antiperspirant salts are known in the art. For example, U.S. Pat. No. 4,120,948, Shelton, issued Oct. 17, 1978 and U.S. Pat. No. 3,792,068, Luedders et al., issued Feb. 12, 1974, both incorporated by reference herein, disclose complexes of aluminum, zirconium, and amino acids such as glycines. These complexes and other similar compleses with glycine amino acids are commonly known as ZAG complexes. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Also useful are the ZAG complexes disclosed in G. P. Patent Application 2,144,992, Callaghan et al., published Mar. 20, 1985. These ZAG actives, when analyzed by high pressure gel permeation chromatography, exhibit a distribution pattern having four or more successive peaks or "bands" where the height ratio of Banks IV to III is greater than 2:1.

More preferred are ZAG actives which have a total area under the curve of bands I and II of less than about 10%, preferably less than about 5%, more preferably less than about 2% and most preferably less than about 1%.

Preferred ZAG complexes can be formed by
(A) co-dissolving in water
(1) one part $Al_2(OH)_{6-m}Q_m$, wherein Q is an anion selected from the group consisting of chloride, bromide,, and iodide; and m is from about 0.8 to about 2.0;
(2) x parts $ZrO(OH)_{2-a}Q_a \cdot nH_2O$, where Q is chloride, bromide, or iodide; a is from about 1 to about 2; n is from about 1 to about 8; and x is from about 0.16 to about 1.2;
(3) p parts neutral amino acid selected from the group consisting of glycine, dl-tryptophane, dl-β-phenylalanine, dl-valine, dl-methionine, and β-alanine, and where p is from about 0.06 to about 0.53;
(B) co-drying the resultant mixture to a friable solid; and
(C) reducing the resultant dried inorganic-organic antiperspirant complex to a particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U. S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the appropriate general formula $[Al_2(OH)_4Cl][H_2CNH_2\text{-}COOH]$. All of these patents are incorporated by reference herein.

Of all of the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and the ZAG-type complexes wherein the zirconium salt is $ZrO(OH)_2$.$_aCl_a.nH_2O$ wherein a is from about 1.5 to about 1.87 and n is from about 1 to about 7, the aluminum salt is $Al_2$.$(OH)_5Cl.2H_2O$, and the amino acid is glycine.

The most preferred antiperspirant actives useful in the compositions of the present invention are antiperspirant actives with enhanced efficacy due to improved molecular distribution. Aluminum chlorhydroxide salts, zirconyl hydroxychloride salts, and mixtures thereof having improved molecular distributions are known, having been disclosed, for example, in the following documents, all incorporated by reference herein: U.S. Pat. No. 4,359,456, Gosling et al., issued Nov. 16, 1982; European Published Patent Application, 183,171, Armour Pharmaceutical Company, published Jun. 4, 1986; British Patent Specification 2,048,229, The Gillette Company, published Dec. 10, 1980; European Published Patent Application 191,628, Unilever PLC, published Aug. 20, 1986; and British Patent Specification 2,144,992, The Gillette Company, published Mar. 20, 1985.

The improved molecular distribution is determined by the known analysis method called gel permeation chromatography. This analysis method is described, for example, in several of the above-incorporated patent specifications as well as in European Published Patent Application 7,191, Unilever Ltd., published Jan. 23, 1980, the disclosures of which are incorporated herein. It is preferred for purposes of the present invention that the antiperspirant actives utilized have enhanced efficacy due to improved molecular distribution with a ratio of peak 4 to peak 3 greater than about 0.1:1 as determined by gel permeation chromatography. This ratio, as is recognized by one skilled in the art, relates to the relative area under those two peaks as measured by the gel permeation chromatography analysis method.

Highly desirable antiperspirant salts for use herein include aluminum chlorohydrex (sold under the name Rehydrol ®, by Reheis Chemical Company), aluminum chlorohydrex PEG, aluminum chlorohydrex PG, aluminum sesquichlorohydrate, aluminum sesquichlorohydrex PEG, aluminum sesquichlorohydrex PG, and mixtures thereof, particularly aluminum sesquichlorohydrate.

The antiperspirant active material is present in the liquid antiperspirant compositions of the present invention at a level of from about 10% to about 70%, preferably from about 15% to about 60%. These weight percentages are calculated on an anhydrous metal salt basis (exclusive of glycine, the salts of glycine, or other complexing agents).

Non-volatile Silicone Fluid

Another essential component of the present invention is a non-volatile silicone fluid component. In addition to serving as a vehicle for antiperspirant active delivery to the skin, this component can act as an emollient, can inhibit formation of chalk-like residue common in many conventional liquid antiperspirant compositions, and can inhibit rub-off of the antiperspirant active material in use. The non-volatile fluid component can comprise one or more silicone fluid materials, but should have an "average" viscosity within the range of from about 10 centistokes to about 50 centistokes, preferably from 15 centistokes to about 35 centistokes, at 25° C., more preferably from about 18 centistokes to about 30 centistokes. By "average viscosity" is meant that the non-volatile silicone fluid component can have one or more non-volatile silicone fluids outside of the specified range of about 10 to about 50 centistokes, but the overall, i.e., the weighted average, viscosity should be within said range. Viscosity can be measured by a Brookfield ® cone and plate viscometer, or other suitable method. By "non-volatile" silicone fluid, as is well known and understood in the art, is meant that the silicone fluids of which the non-volatile silicone fluid component is comprised are not readily vaporizable (i.e., they do not exhibit an appreciable vapor pressure) at ambient temperatures (particularly at about 20° C. to 25° C.).

The non-volatile silicone fluids that may be used in the present compositions include polyalkyl siloxanes, polyalkylaryl siloxanes, and polyether siloxane copolymers, and mixtures thereof. Preferred non-volatile silicone fluids are linear polyalkyl siloxanes, especially linear polydimethyl siloxanes (i.e., dimethicone). These siloxanes are available, for example, from the General Electric Company (Silicone Products Division, Waterford, N.Y., USA) in the Viscasil TM series and from Dow Corning Corporation (Midland, Mich., USA), as the Dow Corning 200 Fluid series.

Other non-volatile silicone fluids that can be used include polymethylphenylsiloxanes. These siloxanes are available, for example, from the General Electric Company as SF 1075 methyl phenyl fluid or from Dow Corning as 556 Fluid.

A polyether siloxane copolymer that may be used is, for example, a dimethyl polyoxyalkylene ether copolymer fluid. Such copolymers are available, for example, from the General Electric Company as SF-1066 organosilicone surfactant.

The non-volatile silicone fluid component is present in the compositions hereof in an amount ranging from about 25% to about 75%, preferably from about 35% to about 70%, more preferably about 45% to about 65% of the composition.

Suspension Agent

Another essential component of the present compositions is a suspension agent. Such suspension agent is present at a level of from about 1% to about 15%, preferably from about 2% to about 8%.

Clays and colloidal pyrogenic silica pigments are the preferred materials for use as suspension agents. Colloidal silica is available commercially as Cab-O-Sil ®, a submicroscopic particulated pyrogenic silica.

Clay suspension agents suitable for use in the compositions of the present invention are selected from the group consisting of montmorillonite clays and hydrophobically treated montmorillonite clays. Montmorillonite clays are those which contain the mineral montmorillonite and are characterized by having a suspending lattice. Examples of these clays include the bentonites, hectorites, and colloidal magnesium aluminum silicates. Clay materials are typically made hydrophobic by treatment with a cationic surfactant, such as quaternary ammonium cationic surfactants (e.g., ditallow dimethyl ammonium chloride, i.e., quaternium-18).

Bentonite is colloidal, hydrated aluminum silicate obtained from montmorillonite and has the formula $Al_2O_3 4SiO_2 \cdot H_2O$. A more detailed discussion of bentonites can be found in the Kirk-Othmer Encyclopedia of Chemical Technology, 2nd. ed., Vol 3(1964), pp 339-360, published by Interscience Publishers, which is incorporated herein by reference.

Hectorite, also a montmorillonite clay, differs from bentonite in that there is almost a complete substitution of aluminum in the lattice structure of bentonite by magnesium. In addition, hectorites contain lithium and fluorine. Laponite TM is an example of a commercially available synthetic hectorite marketed by Laporte Indusries, Ltd.

The magnesium aluminum silicates are complexes of colloidal magnesium aluminum silicate richer in magnesium than aluminum. Magnesium aluminum silicates are commercially available as Veegum TM (R. T. Vanderbilt Co.).

Preferred clay suspension agents for use in the present invention include hydrophobically treated montmorillonite clays, e.g., hydrophobic bentonites available under the tradename of Bentone TM. Bentone TM is prepared by reacting bentonite in a cation exchange system with an amine. Different amines are reacted to obtain a variety of Bentones, which may also differ in proportions of $SiO_2$, MgO and $Al_2O_4$. Specific examples of Bentones TM within the scope of the present invention are Bentone TM 38, Bentone TM 34, Bentone TM 27, Bentone TM 14, and Bentone TM LT, all of which have a particle size of below about 5 microns and are commercially available from the NL Industries, Inc.

The compositions that utilize hydrophobically-treated hectorite and bentonite clays to suspend the antiperspirant active material will also generally include a clay activator. Many such clay activators, as well as the levels of use in liquid antiperspirant compositions, are known in the art. Such activating materials include, for example, propylene carbonate, ethanol, and mixtures thereof. Typically, the level of clay activator will be from about 25% to about 75% of the weight of the clay, more typically from about 40% to about 60% of the weight of the clay.

Optional Emollients

The present antiperspirant composition may comprise optional emollients such as volatile silicone fluids as well as non-silicone emollients such as mineral oil, paraffin oils, etc. When present, however, such optional emollients do not total more than about 15% of the composition, and preferably no more than about 10% of the composition. To minimize any incidence of skin irritation, the compositions preferably contain less than about 5% of such skin-irritating emollients. Such optional emollients may be included for a variety of reasons, including both cost-saving, and cosmetic purposes. In particular, it may be desirable to include a low amount of mineral oil or other paraffinic oil, such as from about 1% to about 12%.

Typical volatile silicone materials include, but are not limited to, D4-D5 cyclomethicones, phenethyl pentamethyl disiloxane, and mixtures thereof. Volatile dimethicone fluid is also contemplated herein.

Other Optional Components

The compositions of the present composition may also comprise a number of non-emollient optional components to provide cosmetic or aesthetic benefits. For example, preservatives, deodorant actives, such as antimicrobials or bacteriocides, perfumes, coloring agents, fillers, dyes and thickeners may be used. Suitable thickening agents include carboxymethyl cellulose, and polyethylene powder, such as Microthene ® powder, a polyethylene powder manufactured by U.S.I. Chemicals (New York, N.Y., USA), having a mean particle diameter of less than about 20 microns.

These optional components should be chosen so as not to unduly interfere with the antiperspirant efficacy and the composition stability. Such optional components are generally present in the compositions of the present invention at a level of from about 0.01% to about 20%.

Products

The present compositions are preferably in the form of a low-viscosity roll-on liquid. However, the present invention may be applicable to other liquid antiperspirant product types, such as aerosol sprays. Products formulated as aerosols will also comprise a propellant material. Any of the commonly used propellants in the antiperspirancy art are suitable. The propellant can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, butane and isobutane, used singly or admixed. Isobutane, used singly or admixed with other hydrocarbons, is preferred.

The amount of the propellant gas is governed by normal factors as are well known in the aerosol art. The composition described previously herein serves as the concentrate and comprises from about 5% to about 80%, preferably 7% to about 45%, more preferably from about 20% to about 40%, of the total aerosol composition while the propellant comprises from about 20% to about 95%, preferably from about 55% to about 93%, more preferably from about 60% to about 80%.

If a propellant such as dimethylether utilizes a vapor pressure suppressant (e.g., trichloroethane or dichloromethane) the amount of suppressant is included as part of the propellant.

Although the non-volatile silicone or other silicone fluid, or fluid emollient (such as paraffinic oil) may suitably serve as a carrier liquid in the compositions hereof, additional materials may also be used, particularly in the case of aerosol compositions. The carrier liquid can aid efficacy by keeping the antiperspirant compound in contact with the skin so that it does not rub off or wash off. Examples of additional materials are carboxylic esters like isopropyl myristate and isopropyl palmitate; alcohols such as lauryl alcohol, hexadecyl alcohol, and oleyl alcohol; carboxylic acids such as lauric and oleic acid; and lanolin and its derivatives such as acetylated lanolin. Other operable carrier liquids are more hydrophilic than the above-mentioned compounds, for example, organic compounds containing multiple ester groups. This includes, but is not limited to, diesters of dibasic organic acids. Examples of compounds containing multiple ester groups that are suitable for the instant invention are di-n-butyl phthalate, diethyl sebacate, diisopropyl adipate, and ethyl ethylcarbomethyl phthalate [ortho $C_2H_5OOC$—O—$COOCH_2COOC_3H_5$].

Still other operable carrier liquids are even more hydrophilic than these esters. Among them are polyethylene glycol monolaurate and butoxy-polyoxyethylene oxypropylene glycols (the Ucon 50 HB series; trade mark—Union Carbide).

Among these various carrier liquids, carboxylic esters having from about 12 to about 16 carbon atoms are preferred. As described supra, they can be either aliphatic or aromatic and can contain either one ester group or multiple ester groups. Especially preferred are di-n-butyl phthalate, diethyl sebacate, diisopropyl adipate, isopropyl myristate and ethyl ethylcarbomethyl phthalate.

These additional carrier liquids, if used, will typically be present in amounts from about 1% to about 15% of the total aerosol composition.

The present compositions may also contain low levels of high molecular weight polymers similar to those described in U.S. Pat. No. 4,152,416, May 1, 1979 to Spitzer et al., incorporated herein by reference, especially in the case of aerosol compositions. These polymeric materials are used at a level of from about 0.005% to 5% of the total aerosol composition. A preferred material is polyvinylisobutyl ether.

Methods of Manufacture

The antiperspirant compositions of the present invention may be manufactured using methods known in the art. In making the compositions, the antiperspirant composition ingredients are typically well-mixed and milled. Aerosol propellant, if applicable, can be included according to standard industry practices. The remaining components are then added to the composition using conventional formulation methods.

Method for Preventing Perspiration and Malodor

The present invention also provides methods for treating or preventing perspiration and malodor associated with human underarm perspiration. These methods comprise applying a safe and effective amount of the liquid antiperspirant compositions of the present invention to the skin in the axillary area of a human. The term a "safe and effective amount" as used herein, is an amount which is effective in eliminating or substantially reducing the production of perspiration which ultimately generates the malodors detected through formation of pungent fatty acids, while being safe for human use at a reasonable risk/benefit ratio.

The liquid antiperspirant compositions of the present invention provide excellent cosmetic attributes both on application and throughout use. They are non-sticky, non-greasy, and provide a dry feel upon application to the skin. The compositions have low incidence of staining of clothes. In addition, the present compositions do not leave substantial levels of white, chalky residue on skin upon dry down, have relatively low incidence of rub-off, and facilitate maintanance of the antiperspirant active material on the skin throughout the in-use period.

The following examples illustrate the present invention. It will be appreciated that other modifications of the present invention within the skill of those in the antiperspirant formulation art can be undertaken without departing from the spirit and scope of this invention.

All parts, percentages, and ratios herein are by weight unless otherwise specified.

EXAMPLES 1-2

The following compositions are liquid antiperspirant compositions that are useful for roll-on application and are representative of the present invention.

|  | Example Number (Wt. %) | |
| --- | --- | --- |
|  | 1 | 2 |
| Dimethicone (20 cs) | 62.7 | 43.9 |
| Dimethicone (50 cs) |  | 8.8 |
| Light mineral oil (about 20 cs) at 25° C.) |  | 10.0 |
| Bentone TM-38 Clay[1] | 3.5 | 3.5 |
| Propylene Carbonate | 1.6 | 1.6 |
| Polyethylene powder[2] | 4.0 |  |
| ZAG antiperspirant active | 26.7 | 26.7 |
| Perfume | 0.02 | 0.02 |

[1] A quaternium-18 treated hectorite clay available from NL Chemicals Division of NL Industries, Inc. (Hightstown, NJ, USA)
[2] Microthene ® polyethylene powder, particle diameter less than about 20 microns, available from U.S.I. Chemicals (New York, NY, USA).

The composition is prepared as follows. The dimethicone material or materials are added to a batch tank, followed by the mineral oil, polyethylene powder and then the Bentone 38 clay, and then mixed for 10 minutes with a rotary mixer. The propylene carbonate is added and the mixture is mixed for an additional 5 minutes. The ZAG antiperspirant active is added and the mixture is mixed for another 10 minutes. Perfume is added and the mixture is mixed for 5 additional minutes. The batch of this liquid is milled to about 750 cps and added to conventional roll-on bottles known in the art. The liquid composition can then be applied to the underarm skin of a human to effectively inhibit perspiration and underarm malodor resulting from perspiration.

The antiperspirant composition provides excellent antiperspirancy efficacy with good product aesthetics and in-use characteristics, including low skin irritation.

EXAMPLES 3-4

Aerosol antiperspirant compositions are prepared by first preparing the liquid antiperspirant compositions of Examples 1 (Example 3) and Example 2 (Example 4), as the aerosol antiperspirant concentrates, and are then combined with A-46 volatile aerosol propellant (87% isobutane/13% propane) in a conventional aerosol container. Each of the aerosol compositions contains 70% of the aerosol propellant and 30% of the aerosol antiperspirant concentrate.

What is claimed is:

1. A liquid antiperspirant composition with reduced incidence of skin irritation comprising:
   (a) from about 10% to about 70%, by weight, of an antiperspirant active material;
   (b) from about 1% to about 15%, by weight, of a suspension agent component;
   (c) from 0% to about 15%, by weight, of a volatile silicone fluid; and
   (d) from about 25% to about 75%, by weight, of a non-volatile silicone fluid having an average viscosity of from about 10 centistokes to about 50 centistokes at 25° C.

2. A liquid antiperspirant as in claim 1, wherein the antiperspirant active material is a zirconium aluminum complex.

3. A liquid antiperspirant as in claim 2, wherein the nonvolatile silicone fluid is a polyalkyl siloxane.

4. A liquid antiperspirant as in claim 3, wherein said nonvolatile silicone fluid comprises dimethicone.

5. A liquid antiperspirant as in claim 1, wherein the amount of the antiperspirant active material is from about 15% to about 60%, the amount of the volatile silicone fluid is from 0% to about 5%, and the amount of the nonvolatile silicone fluid is from about 35% to about 70%.

6. A liquid antiperspirant as in claim 4, wherein the amount of the antiperspirant active material is from about 15% to about 60%, the amount of the volatile silicone fluid is from 0% to about 5%, and the amount of the nonvolatile silicone fluid is from about 45% to about 65%.

7. A liquid antiperspirant as in claim 5, wherein said nonvolatile silicone fluid has an average viscosity of from about 15 centistokes to about 35 centistokes at 25° C.

8. A liquid antiperspirant as in claim 6, wherein said nonvolatile silicone fluid has an average viscosity of from about 18 centistokes to about 30 centistokes at 25° C.

9. A liquid antiperspirant as in claim 1, further comprising from about 1% to about 12%, by weight, of a non-volatile paraffinic oil.

10. A liquid antiperspirant as in claim 9, further comprising from about 1% to about 12%, by weight, of a non-volatile paraffinic oil.

11. A liquid aerosol antiperspirant composition with reduced incidence of skin irritation comprising:
   I. from about 5% to about 80%, by weight of the composition, of an antiperspirant concentrate comprising:
      (a) from about 10% to about 70%, by weight of the concentrate, of an antiperspirant active material;
      (b) from about 1% to about 15%, by weight of the concentrate, of a suspension agent component;
      (c) from 0% to about 15%, by weight of the concentrate, of a volatile silicone fluid; and
      (d) from about 25% to about 75%, by weight of the concentrate, of a non-volatile silicone fluid having a viscosity of from about 10 centistokes to about 50 centistokes at 25° C.; and
   II. from about 20% to about 95%, by weight of the composition, of an aerosol propellant.

12. A liquid antiperspirant as in claim 11, wherein the antiperspirant active material is a zirconium aluminum complex.

13. A liquid antiperspirant as in claim 12, wherein the nonvolatile silicone fluid is a polyalkyl siloxane.

14. A liquid antiperspirant as in claim 13, wherein said nonvolatile silicone fluid comprises dimethicone.

15. A liquid antiperspirant as in claim 11, wherein the amount of the antiperspirant active material is from about 15% to about 60%, the amount of the volatile silicone fluid is from 0% to about 5%, and the amount of the nonvolatile silicone fluid is from about 35% to about 70%.

16. A liquid antiperspirant as in claim 14, wherein the amount of the antiperspirant active material is from about 15% to about 60%, the amount of the volatile silicone fluid is from 0% to about 5%, and the amount of the nonvolatile silicone fluid is from about 45% to about 65%.

17. A liquid antiperspirant as in claim 15, wherein said nonvolatile silicone fluid has a viscosity of from about 15 centistokes to about 35 centistokes at 25° C.

18. A liquid antiperspirant as in claim 16, wherein said nonvolatile silicone fluid has a viscosity of from about 18 centistokes to about 30 centistokes at 25° C.

19. A liquid antiperspirant as in claim 11, further comprising from about 0.1% to about 15%, by weight, of a non-volatile paraffinic oil.

20. A liquid antiperspirant as in claim 19, further comprising from about 0.1% to about 15%, by weight, of a non-volatile paraffinic oil.

* * * * *